United States Patent
Gupta et al.

(10) Patent No.: US 8,158,406 B2
(45) Date of Patent: Apr. 17, 2012

(54) METHOD FOR THE ENANTIOSELECTIVE ENZYMATIC REDUCTION OF KETO COMPOUNDS USING R-SPECIFIC OXIDOREDUCTASE

(75) Inventors: Antje Gupta, Wiesbaden (DE); Maria Bobkova, Idstein (DE); Anke Tschentscher, Wiesbaden (DE)

(73) Assignee: IEP GmbH, Wiesbaden (DE)

( * ) Notice: Subject to any disclaimer, the term of this patent is extended or adjusted under 35 U.S.C. 154(b) by 789 days.

(21) Appl. No.: 11/816,708

(22) PCT Filed: Feb. 21, 2006

(86) PCT No.: PCT/EP2006/001562
§ 371 (c)(1),
(2), (4) Date: Dec. 5, 2007

(87) PCT Pub. No.: WO2006/087253
PCT Pub. Date: Aug. 24, 2006

(65) Prior Publication Data
US 2008/0153140 A1    Jun. 26, 2008

(30) Foreign Application Priority Data
Feb. 21, 2005 (AT) .................................. A 285/2005

(51) Int. Cl.
*C12P 41/00* (2006.01)

(52) U.S. Cl. ........................................................ 435/280

(58) Field of Classification Search .................. None
See application file for complete search history.

(56) References Cited

U.S. PATENT DOCUMENTS

| | | | |
|---|---|---|---|
| 6,037,158 A | 3/2000 | Hummel et al. | |
| 7,202,069 B2 * | 4/2007 | Kudoh et al. | 435/190 |
| 2004/0265978 A1 | 12/2004 | Gupta et al. | |

FOREIGN PATENT DOCUMENTS

| | | |
|---|---|---|
| CA | 2529583 | 12/2004 |
| EP | 0796914 | 9/1997 |
| EP | 1179595 | 2/2002 |
| WO | WO-02/086126 | 10/2002 |
| WO | WO-03/078615 | 9/2003 |
| WO | WO-2004/111083 | 12/2004 |

OTHER PUBLICATIONS

Yang H et al., "The enantiomeric purity of alcohols formed by enzymatic reduction of ketones can be improved by optimisation of the temperature and by using a high co-substrate concentration," BBA—General Subjects, Elsevier Science Publishers, NL, vol. 1336, No. 1, Jul. 19, 1997, pp. 51-58, XP004276020.

* cited by examiner

*Primary Examiner* — Sandra Saucier
(74) *Attorney, Agent, or Firm* — Birch, Stewart, Kolasch & Birch, LLP

(57) ABSTRACT

The present invention relates to a process for the enantioselective enzymatic reduction of keto compounds, in particular of 4-halo-3-oxobutyric acid esters, to the corresponding R-alcohols or S-4-halo-3-hydroxybutyric acid esters, respectively, using an R-specific oxidoreductase in the presence of a cofactor.

15 Claims, No Drawings

METHOD FOR THE ENANTIOSELECTIVE ENZYMATIC REDUCTION OF KETO COMPOUNDS USING R-SPECIFIC OXIDOREDUCTASE

This application is the National phase under 35 U.S.C. §371 of PCT International Application No. PCT/US2006/001562 filed on Feb. 21, 2006, which designates the United States of America. This application also claims priority under 35 U.S.C. §119(a) on Patent Application No. A 285/2005 filed in Austria on Feb. 21, 2005. The entire contents of each of the above documents is hereby incorporated by reference.

The present invention relates to a process for the enantioselective enzymatic reduction of keto compounds, in particular of 4-halo-3-oxobutyric acid esters, to the corresponding R-alcohols or S-4-halo-3-hydroxybutyric acid esters, respectively.

Carbonyl reductases (further names: alcohol dehydrogenases, oxidoreductases) are known as catalysts for the reduction of carbonyl compounds and for the oxidation of secondary alcohols, respectively. Said enzymes require a coenzyme, e.g., NAD(P)H. The reduction of ketones with the carbonyl reductase obtained from *Lactobacillus kefir* and with the coenzyme NADPH is known, for example, from U.S. Pat. No. 5,342,767.

Optically active hydroxy compounds are valuable chirons with broad applicability for the synthesis of pharmacologically active compounds, aromatic substances, pheromones, agricultural chemicals and enzyme inhibitors. S-4-Halo-3-hydroxybutyric acid esters are, for example, important intermediates for the synthesis of HMG-CoA reductase inhibitors, D-carnitine and others.

Enantioselective enzymes are known which are capable, for example, of reducing 4-halo-3-oxobutyric acid esters to the corresponding S-4-halo-3-hydroxybutyric acid esters. As examples, the following can be mentioned:

reductases from baker's yeast (D-enzyme-1, D-enzyme-2, J. Am. Chem. Soc. 107, 2993-2994, 1985);

aldehyde reductase 2 from *Sporobolomyces salmonicolor* (Appl. Environ. Microbiol. 65, 5207-5211, 1999);

ketopantothenic acid ester reductase from *Candida macedoniensis* (Arch. Biochem. Biophys. 294, 469-474, 1992);

reductase from *Geotrichum candidum* (Enzyme Mircrob. Technol. 14, 731-738, 1992);

carbonyl reductase from *Candida magnoliae* (WO 98/35025);

carbonyl reductase from *Kluyveromyces lactis* (JP-A Hei 11-187869);

β-ketoacyl-acyl carrier protein reductase of type II fatty acid synthetase (JP-A 2000-189170);

(R)-2-octanol dehydrogenase from *Pichia finlandica* (EP 1179595 A1);

R-specific secondary alcohol dehydrogenases from organisms of the genus *Lactobacillus* (*Lactobacillus kefir* (U.S. Pat. No. 5,200,335), *Lactobacillus brevis* (DE 19610984 A1) (Acta Crystallogr D Biol Crystallogr. 2000 December; 56 Pt 12:1696-8), *Lactobacillus minor* (DE10119274); *Pseudomonas* (U.S. Pat. No. 5,385,833)(Appl Microbiol Biotechnol. 2002 August; 59(4-5):483-7. Epub 2002 Jun. 26, J. Org. Chem. 1992, 57, 1532).

With the exception of enzymes from *Pseudomonas*, from *Lactobacillus* and from *Pichia finlandica* (EP 1179595 A1), the known enzymes usually do not accept secondary alcohols as substrates and also fail to catalyze the oxidation of secondary alcohols.

In an industrial enzymatic reduction process, said enzymes thus have to be coupled to a further enzyme responsible for the regeneration of the cofactor NADH or NADPH, respectively. Such enzymes suitable for the regeneration of NAD(P)H are formate dehydrogenase, glucose dehydrogenase, malate dehydrogenase, glycerol dehydrogenase and alcohol dehydrogenase, which preferably are expressed together with the enzyme for the reduction of 4-halo-3-oxobutyric acid esters.

It has been possible to demonstrate that recombinant cells of *Escherichia coli*, which, for example, simultaneously express the gene for the carbonyl reductase from *Candida magnoliae* as well as the gene for the glucose dehydrogenase from *Bacillus megaterium*, can be used efficiently in an aqueous/organic two-phase system, wherein substrate concentrations of >40% (by weight) have been realized (Appl Microbiol Biotechnol (2001), 55; 590-595, Ann N Y Acad. Sci. 1998 Dec. 13; 864:87-95).

Processes with enzymes from the group of Lactobacillales (*Lactobacillus minor*; DE 10119274) have so far been implemented successfully using a substrate-coupled coenzyme regeneration with 2-propanol, wherein the reduction of insoluble substrates has been realized also at high concentrations by employing aqueous/organic two-phase systems (U.S. Pat. No. 5,342,767, DE10119274).

When applying the substrate-coupled coenzyme regeneration with 2-propanol or 2-butanol, respectively, the low tolerance of most enzymes toward 2-propanol and 2-butanol has basically been regarded as limiting. Usually, concentrations of 2-propanol which are clearly below 10% by volume are used.

In the prior art, no methods are known wherein the use of R-specific oxidoreductases from yeasts with a substrate-coupled coenzyme regeneration with 2-propanol and/or 2-butanol is described.

Due to the limited use of the cosubstrate 2-propanol, only unsatisfactory substrate concentrations and conversion rates have been achieved (Angew Chemie Int Ed Engl 2002, 41: 634-637, Biotechnol Bioeng 2004 Apr. 5; 86 (1): 55-62).

Recently, it has been possible to isolate an S-specific, medium-chain alcohol dehydrogenase from *Rhodococcus ruber*, which is still stable and active also in case of substantially higher concentrations of 2-propanol of 50-80% (percentage by volume). (Biotechnol Bioeng 2004 Apr. 5; 86 (1): 55-62), WO 03/078615).

The invention aims at overcoming said disadvantages and relates to a process for the enantioselective enzymatic reduction of keto compounds of general formula I $$R_1-C(O)-R_2 \quad (I)$$

in which R1 stands for one of the moieties

1) —$(C_1-C_{20})$-alkyl, wherein alkyl is linear-chain or branched,
2) —$(C_2-C_{20})$-alkenyl, wherein alkenyl is linear-chain or branched and optionally contains up to four double bonds,
3) —$(C_2-C_{20})$-alkynyl, wherein alkynyl is linear-chain or branched and optionally contains up to four triple bonds,
4) —$(C_6-C_{14})$-aryl,
5) —$(C_1-C_8)$-alkyl-$(C_6-C_{14})$-aryl,
6) —$(C_5-C_{14})$-heterocycle which is unsubstituted or substituted one, two or three times by —OH, halogen, —$NO_2$ and/or —$NH_2$, or
7) —$(C_3-C_7)$-cycloalkyl,
wherein the moieties mentioned above under 1) to 7) are unsubstituted or substituted one, two or three times, independently of each other, by —OH, halogen, —$NO_2$ and/or —$NH_2$,
and $R_2$ stands for one of the moieties
8) —$(C_1-C_6)$-alkyl, wherein alkyl is linear-chain or branched, 9) —($C_2$-$C_6$)-alkenyl, wherein alkenyl is linear-chain or branched and optionally contains up to three double bonds,
10) —($C_2$-$C_6$)-alkynyl, wherein alkynyl is linear-chain or branched and optionally contains two triple bonds, or
11) —($C_1$-$C_{10}$)-alkyl-C(O)—O—($C_1$-$C_6$)-alkyl, wherein alkyl is linear or branched and is unsubstituted or substituted one, two or three times by —OH, halogen, —$NO_2$ and/or —$NH_2$, wherein the moieties mentioned above under 8) to 11) are unsubstituted or substituted one, two or three times, independently of each other, by —OH, halogen, —$NO_2$ and/or —$NH_2$, which is characterized in that
a liquid, single-phase mixture comprising
(a) at least 5% by weight/by volume of a compound of formula (I),
(b) at least 15% by volume of 2-propanol and/or 2-butanol, and
(c) water
is treated with an R-specific oxidoreductase in the presence of a cofactor in order to form a chiral hydroxy compound of general formula II

$R_1$—CH(OH)—$R_2$ (II)

wherein $R_1$ and $R_2$ have the above-indicated meaning.

The term "aryl" is meant to comprise aromatic carbon moieties having 6 to 14 carbon atoms in the ring. —($C_6$-$C_{14}$)-aryl moieties are, for example, phenyl, naphthyl, e.g., 1-naphthyl, 2-naphthyl, biphenylyl, e.g., 2-biphenylyl, 3-biphenylyl and 4-biphenylyl, anthryl or fluorenyl. Biphenylyl moieties, naphthyl moieties and in particular phenyl moieties are preferred aryl moieties. The term "halogen" means an element from the series of fluorine, chlorine, bromine or iodine. The term "—($C_1$-$C_{20}$)-alkyl" means a hydrocarbon moiety whose carbon chain is linear-chain or branched and contains 1 to 20 carbon atoms, for example, methyl, ethyl, propyl, isopropyl, butyl, tertiary butyl, pentyl, hexyl, heptyl, octyl, nonyl or decanyl. The term "—$C_0$-alkyl" means a covalent bond.

The term "—($C_3$-$C_7$)-cycloalkyl" is meant to comprise cyclic hydrocarbon moieties such as cyclopropyl, cyclobutyl, cyclopentyl, cyclohexyl or cycloheptyl. The term "—($C_5$-$C_{14}$)-heterocycle" denotes a monocyclic or bicyclic 5-membered to 14-membered heterocyclic ring which is partially saturated or completely saturated. N, O and S are examples of heteroatoms. Moieties derived from pyrrole, furane, thiophene, imidazole, pyrazole, oxazole, isoxazole, thiazole, isothiazole, tetrazole, 1,2,3,5-oxathiadiazole-2-oxide, triazolone, oxadiazolone, isoxazolone, oxadiazolidinedione, triazole, substituted by F, —CN, —$CF_3$ or —C(O)—O—($C_1$-$C_4$)-alkyl, 3-hydroxypyrro-2,4-dione, 5-oxo-1,2,4-thiadiazole, pyridine, pyrazine, pyrimidine, indole, isoindole, indazole, phthalazine, quinoline, isoquinoline, quinoxaline, quinazoline, cinnoline, carboline and benz-anellated, cyclopenta-, cyclohexa- or cyclohepta-anellated derivatives of said heterocycles are examples for the term "—($C_5$-$C_{14}$)-heterocycle". The moieties 2- or 3-pyrrolyl, phenylpyrrolyl such as 4- or 5-phenyl-2-pyrrolyl, 2-furyl, 2-thienyl, 4-imidazolyl, methyl-imidazolyl, e.g., 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g., 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl or dihydropyridinyl, pyrrolidinyl, e.g., 2- or 3-(N-methylpyrrolidinyl), piperazinyl, morpholinyl, thiomorpholinyl, tetrahydrothienyl or benzodioxolanyl are particularly preferred.

The present invention is based on the knowledge that, if R-specific alcohol dehydrogenases or oxidoreductases, respectively, are employed, these can also be used with concentrations of 2-propanol and/or 2-butanol of well above 15% by volume and particularly above 25% by volume.

This opens up the possibility of enzymatically reducing in an enantioselective manner also poorly water-soluble substrates such as, for example, 4-halo-3-oxobutyric acid ester at high concentrations in a homogeneous, aqueous/organic system. This is advantageous particularly if the nascent chiral alcohol is to be supplied in a continuous process directly, without previous isolation, to a consecutive reaction occurring in a single-phase, aqueous/organic reaction mixture.

This happens, for example, during the enantioselective reduction of 4-chloroacetoacetate wherein the nascent product S-4-chloro-3-hydroxybutyric acid ethyl ester can be added in such a homogeneous reaction mixture directly to a cyanidation process and can be processed further to (R)-4-cyano-3-hydroxybutyric acid ethyl ester (WO 03/097581 A1).

The terms "R-specific oxidoreductase" and alcohol dehydrogenase, respectively, are meant to comprise those which reduce unsubstituted carbonyl compounds such as, for example, 2-butanone, 2-octanone or acetophenone preferably to the corresponding R-hydroxy compounds such as, for example, R-2-butanol, R-2-octanol or R-2-phenylethanol.

The R-specific oxidoreductase used according to the invention is preferably of a microbial origin and stems in particular from bacteria of the group of Lactobacillales, particularly of the genus *Lactobacillus*, e.g., *Lactobacillus kefir* (U.S. Pat. No. 5,200,335), *Lactobacillus brevis* (DE 19610984 A1) (Acta Crystallogr D Biol Crystallogr. 2000 December; 56 Pt 12:1696-8), *Lactobacillus minor* (DE10119274) or *Leuconostoc carnosum*, or from yeasts, particularly of the genera *Pichia, Candida, Pachysolen, Debaromyces* or *Issatschenkia*, particularly preferably from *Pichia finlandica* (EP 1 179 595 A1).

In the process according to the invention, NAD(P)H is preferably used as the cofactor. The term "NADPH" refers to reduced nicotinamide adenine dinucleotide phosphate. The term "NADP" refers to nicotinamide adenine dinucleotide phosphate.

An embodiment of the process according to the invention is characterized in that the liquid, single-phase mixture contains at least 25% by volume of 2-propanol and/or 2-butanol if an oxidoreductase of a bacterial origin is used.

A further embodiment of the process according to the invention consists in that the liquid, single-phase mixture contains between 25 and 90% by volume, in particular between 35 and 70% by volume, of 2-propanol and/or 2-butanol.

The compound of general formula (I) is contained in the liquid, single-phase mixture preferably in an amount of between 5 and 50% by weight/by volume, in particular of between 15 and 50% by weight/by volume.

If an oxidoreductase from yeasts is used, the liquid, single-phase mixture preferably contains at least 15% by volume of 2-propanol.

In the process according to the invention, ethyl-4-chloroacetoacetate, methylacetoacetate, ethyl-3-oxovaleriate, 4-hydroxy-2-butanone, ethylpyruvate, 2,3-dichloroacetophenone, 1-[3,5-bis(trifluoromethyl)phenyl]ethane-1-one, acetophenone, 2-octanone, 3-octanone, 2,5-hexanedione, 1,4-dichloro-2-butanone, acetoxyacetone, phenacylchloride, ethyl-4-bromoacetoacetate, 1,1-dichloroacetone, 1,1,3-trichloroacetone or 1-chloroacetone is preferably used as the compound of general formula (I).

In the process according to the invention, the enzyme can be used either in a completely purified or partially purified state or while being contained in cells. In doing so, the cells used can be provided in a native, permeabilized or lysed state.

10 000 to preferably 10 million units (U) of oxidoreductase can be used per kg of compound of formula I to be reacted. Thereby, the enzyme unit 1 U corresponds to the enzyme amount which is required for reacting 1 μmol of the compound of formula I per minute (min).

A buffer, e.g., a potassium phosphate, tris/HCl or triethanolamine buffer having a pH value of 5 to 10, preferably a pH value of 6 to 9, can be added to the water.

In addition, the buffer can contain ions for stabilizing the enzyme, for example magnesium ions.

Moreover, a further stabilizer of alcohol dehydrogenase such as, for example, glycerol, sorbitol, 1,4-DL-dithiothreitol (DTT) or dimethyl sulfoxide (DMSO) can be used in the process according to the invention.

The concentration of the cofactor NAD(P)H, based on the aqueous phase, ranges from 0.001 mM to 1 mM, in particular from 0.01 mM to 0.1 mM.

The temperature ranges, for example, from approximately 10° C. to 60° C., preferably from 20° C. to 35° C.

One process variant for increasing the conversion of the keto compound consists in that the oxidized cosubstrate is removed either gradually or continuously from the reaction mixture during the process.

Furthermore, a fresh cosubstrate, enzyme or cofactor can be added gradually or continuously to the reaction batch.

The process according to the invention is carried out, for example, in a reaction vessel made of glass or metal. For this purpose, the components are transferred individually into the reaction vessel and stirred under an atmosphere of, e.g., nitrogen or air. Depending on the substrate and the compound of formula I which is used, the reaction time lasts from 1 hour to 96 hours, in particular from 2 hours to 24 hours.

Preferred embodiments of the invention are illustrated in further detail by means of the following examples.

The reduction of the compounds of formula 1 is suitably carried out such that the components indicated below are transferred into a reaction vessel and incubated at room temperature while being thoroughly mixed. Upon completion of the reaction, the product can be isolated and purified, depending on solubility, from the aqueous reaction solution by extraction, from the reaction solution by distillation or by a combination of extraction and distillation.

In all the following examples, the enzymes were used in the form of crude extracts.

EXAMPLE 1

Synthesis of (S)-ethyl-4-chloro-3-hydroxybutyric acid

| component | amount | percentage in the reaction volume | concentration |
|---|---|---|---|
| buffer (TEA pH = 7, 2 mM $MgCl_2$,) | 60 ml | | |
| NADP [M = 765 g/mol] | 4.8 mg | | =6.3 μmol =0.015 mM |
| cosubstrate 2-propanol | 200 ml | 50% | |
| ethyl-4-chloroacetoacetate | 80 ml = 96 g | 20% (v/v) 24% (w/v) | 0.58 mol |
| enzyme = R-ADH from L.minor = 1000 U/ml | 60 000 units (60 ml) | | |
| volume | 400 ml | | |
| incubation period | 24 h | | |
| conversion | >99% | | |
| ee-value | >99.9% S | | |
| ttn NADP | 92 950 | | |
| enzyme consumption | 600 000 units/kg | | |

EXAMPLE 2

Synthesis of (R)-methyl-3-hydroxybutyric acid

| component | amount | percentage in the reaction volume | concentration |
|---|---|---|---|
| buffer (TEA pH = 7, 1 mM $MgCl_2$, 10% glycerol) | 300 ml | | |
| NADP [M = 765 g/mol] | 10 mg | | 13 μmol (0.012 mM) |
| cosubstrate 2-propanol | 400 ml | 36.6% | |
| methylacetoacetate M = 116 g/mol, d = 1.077 g/cm³ | 300 ml | 27.5% (v/v) 29.6 (w/v) | 2.7 mol |
| enzyme = R-ADH from L.minor = 1000 U/ml | 90 000 units 90 ml | | |
| volume | 1090 ml | | |
| incubation period | 24 h | | |
| conversion | 99% | | |
| ee-value | >99.9% | | |
| ttn NADP | 207692 | | |
| enzyme consumption | 280 000 U/kg | | |

EXAMPLE 3

Synthesis of ethyl-D-lactate

| component | amount | percentage in the reaction volume | concentration |
|---|---|---|---|
| buffer (TEA pH = 7, 1 mM $MgCl_2$, 10% glycerol) | 170 ml | | |
| NADP [M = 765 g/mol] | 40 mg | | 52 μmol (0.054 mM) |
| cosubstrate 2-propanol | 500 ml | 52% | |
| ethylpyruvate M = 117 g/mol, d = 1.045 | 250 ml | 26% (v/v) 27.2 (w/v) | 2.2 mol |
| enzyme = | 40 000 | | |

EXAMPLE 4

Synthesis of (R)-1,3-butanediol

| component | amount | percentage in the reaction volume | con-centration |
|---|---|---|---|
| buffer (TEA pH = 7, 1 mM MgCl$_2$, 10% glycerol) | 0.5 ml | | |
| NADP [M = 765 g/mol] | 0.1 mg | | 0.13 μmol (0.013 mM) |
| cosubstrate 2-propanol | 4.5 ml | 44% | |
| 4-hydroxy-2-butanone (M = 88.12 gmol) | 5 ml | 48% (v/v) | 0.057 mol |
| enzyme (R-ADH from L.minor) = 1000 U/ml | 250 U (250 μl) | | |
| volume | 10.25 ml | | |
| system: | single-phase | | |
| process operation*: | distilling off the acetone gradual addition of 2-propanol | | |
| incubation period | 24 h | | |
| total consumption of 2-propanol | 13.5 ml | | |
| conversion | 90% | | |
| ee-value | 99% R | | |
| ttn NADP | 438 461 | | |
| enzyme consumption | 750 000 U/kg | | |

*The acetone formed was distilled from the batch twice and subsequently an amount of 2-propanol and enzyme equal to that at the beginning of the reaction was again added to the reaction mixture. In this way, a conversion of 90% could be achieved even in a batch having a substrate concentration of 48%.

EXAMPLE 5

Synthesis of R-2-octanol

| component | amount | percentage in the reaction volume | concentration |
|---|---|---|---|
| buffer (TEA pH = 7, 1 mM MgCl$_2$, 10% glycerol) | 270 ml | | |
| NADP [M = 765 g/mol] | 27 mg | | 35 μmol (=0.023 mM) |
| cosubstrate 2-propanol | 900 ml | 60% | |
| 2-octanone (128 g/mol, d = 0.8) | 300 ml | 20% (v/v) 16% (w/v) | 1.87M |
| enzyme (R-ADH from L.minor) = 1000 U/ml volume | 30 000 units (30 ml) 1500 | | |

(continued)

| component | amount | percentage in the reaction volume | concentration |
|---|---|---|---|
| system: | single-phase | | |
| process operation*: | distilling off the acetone gradual addition of 2-propanol | | |
| incubation period | 24 h | | |
| total consumption of 2-propanol | 1350 ml | | |
| conversion | 97% | | |
| ee-value | 100% R | | |
| ttn NADP | 53 000 | | |
| enzyme consumption | 200 000 U/kg | | |

*The acetone formed was distilled from the batch once and subsequently an amount of 2-propanol and enzyme equal to that at the beginning of the reaction was again added to the reaction mixture. In this way, a conversion of 97% could be achieved even in a batch having a substrate concentration of 20%.

EXAMPLE 6

Synthesis of (R,R)-2,5-hexanediol

| component | amount | percentage in the reaction volume | con-centration |
|---|---|---|---|
| buffer (TEA pH = 6, 1 mM MgCl$_2$, 10% glycerol) | 100 ml | | |
| NADP [M = 765 g/mol] | 5 mg | | 6.5 μmol (0.011 mM) |
| cosubstrate 2-propanol | 325 ml | 56% | |
| 2,5-hexanedione (114 g/mol, d = 1) | 125 ml | 22% (v/v) 22% (w/v) | 1.09 mol |
| enzyme (R-ADH from L.minor) = 1000 U/ml | 25 000 | | |
| volume | 575 ml | | |
| system: | single-phase | | |
| process operation*: | distilling off the acetone gradual addition of 2-propanol | | |
| incubation period | 48 h | | |
| total consumption of 2-propanol | 650 ml | | |
| conversion | 78% | | |
| ee-value | 100% R, R | | |
| ttn NADP | 168 000 | | |
| enzyme consumption | 400 000 U/kg | | |

The acetone formed was distilled from the batch once and subsequently an amount of 2-propanol and enzyme equal to that at the beginning of the reaction was again added to the reaction mixture.

EXAMPLE 7

Synthesis of (S)-ethyl-4-chloro-3-hydroxybutyric acid

| component | amount | percentage in the reaction volume | concentration |
|---|---|---|---|
| buffer (TEA pH = 7, | 2 ml | | |

---

-continued (left column top)

| component | amount | percentage in the reaction volume | con-centration |
|---|---|---|---|
| R-ADH from L.minor = 1000 U/ml | | | |
| volume | 960 ml | | |
| incubation period | 48 h | | |
| conversion | 99% | | |
| ee-value | >99% | | |
| ttn NADP | 42 300 | | |
| enzyme consumption | 160 000 U/kg | | |

-continued

| component | amount | percentage in the reaction volume | concentration |
|---|---|---|---|
| 2 mM MgCl$_2$,) | | | |
| NADP [M = 765 g/mol] | 2 mg | | =2.6 µmol<br>=0.065 mM |
| cosubstrate<br>2-propanol | 30 ml | 65% | |
| ethyl-4-<br>chloroacetoacetate | 8 ml = 9.6 g | 17% (v/v)<br>20% (w/v) | 58 mmol |
| enzyme = R-ADH from<br>Leuconostoc carnosum<br>DSMZ 5576 =<br>1000 U/ml | 67 00 units<br>(6 ml) | | |
| volume | 46 ml | | |
| incubation period | 24 h | | |
| conversion | >99% | | |
| ee-value | >99.9% S | | |
| ttn NADP | 22 300 | | |
| enzyme consumption | 670 000<br>units/kg | | |

EXAMPLE 8

Synthesis of
(1R)-1-[3,5-bis(trifluoromethyl)phenyl]ethane-1-ol

| component | amount | percentage in the reaction volume | concentration |
|---|---|---|---|
| buffer<br>(TEA pH = 8.5,<br>2 mM MgCl$_2$,) | 200 µl | | |
| NAD [M = 663 g/mol] | 0.05 mg | | 0.075 µmol<br>(0.027 mM) |
| cosubstrate<br>2-propanol | 250 µl | 41.6% (v/v) | |
| 1-[3,5 bis-(trifluoro-<br>methyl)phenyl]ethane-1-one<br>[256.15 g/mol] d = 1.422 | 100 µl | 16.6% (v/v) | |
| enzyme = R-<br>ADH from Pichia<br>finlandica (EP1179595A1) | 40 units<br>(0.05 ml) | | 0.56 mmol |
| volume | 600 µl | | |
| incubation period | 24 h | | |
| conversion | 99% | | |
| ee-value | 99.9% R | | |
| ttn NAD | approx. 7500 | | |
| enzyme consumption | 285 000<br>U/kg | | |

The invention claimed is:

1. A process for the enantioselective enzymatic reduction of keto compounds of formula I $$R_1-C(O)-R_2 \quad (I)$$

in which R1 stands for one of the moieties
1) —(C$_1$-C$_{20}$)-alkyl, wherein alkyl is linear-chain or branched,
2) —(C$_2$-C$_{20}$)-alkenyl, wherein alkenyl is linear-chain or branched and optionally contains up to four double bonds,
3) —(C$_2$-C$_{20}$)-alkynyl, wherein alkynyl is linear-chain or branched and optionally contains up to four triple bonds,
4) —(C$_6$-C$_{14}$)-aryl,
5) —(C$_1$-C$_8$)-alkyl-(C$_6$-C$_{14}$)-aryl,
6) —(C$_5$-C$_{14}$)-heterocycle which is unsubstituted or substituted one, two or three times by —OH, halogen, —NO$_2$ and/or —NH$_2$, or
7) —(C$_3$-C$_7$)-cycloalkyl,
wherein the moieties mentioned above under 1) to 7) are unsubstituted or substituted one, two or three times, independently of each other, by —OH, halogen, —NO$_2$ and/or —NH$_2$,
and R$_2$ stands for one of the moieties
8) —(C$_1$-C$_6$)-alkyl, wherein alkyl is linear-chain or branched,
9) —(C$_2$-C$_6$)-alkenyl, wherein alkenyl is linear-chain or branched and optionally contains up to three double bonds,
10) —(C$_2$-C$_6$)-alkynyl, wherein alkynyl is linear-chain or branched and optionally contains two triple bonds, or
11) —(C$_1$-C$_{10}$)-alkyl-C(O)—O—(C$_1$-C$_6$)-alkyl, wherein alkyl is linear or branched and is unsubstituted or substituted one, two or three times by —OH, halogen, —NO$_2$ and/or —NH$_2$,
wherein the moieties mentioned above under 8) to 11) are unsubstituted or substituted one, two or three times, independently of each other, by —OH, halogen, —NO$_2$ and/or —NH$_2$,
comprising
treating a liquid, single-phase mixture comprising
(a) at least 5% by weight/by volume of a compound of formula (I),
(b) at least 15% by volume of 2-propanol and/or 2-butanol, and
(c) water
with an R-specific oxidoreductase in the presence of a cofactor to form achiral hydroxy compound of general formula II $$R_1-CH(OH)-R_2 \quad (II)$$

wherein R$_1$ and R$_2$ have the above-indicated meaning,
and whereby the R-specific oxidoreductase continuously regenerates the cofactor by oxidation of the 2-propanol and/or the 2-butanol.

2. A process according to claim 1, characterized in that the R-specific oxidoreductase is of a microbial origin.

3. A process according to any of claim 1 or 2, wherein the cofactor is selected from NADP or NADPH.

4. A process according to claim 3, wherein the oxidoreductase is of bacterial origin and the liquid, single-phase mixture contains at least 25% by volume of 2-propanol and/or 2-butanol.

5. A process according to claim 1, characterized in that the liquid, single-phase mixture contains between 25 and 90% by volume of 2-propanol and/or 2-butanol.

6. A process according to claim 1 or 5, characterized in that the liquid, single-phase mixture contains the compound of general formula (I) in an amount of between 5 and 50% by weight/by volume.

7. A process according to claim 1 or 5, wherein the compound of the formula (I) is selected from the group consisting of ethyl-4-chloroacetoacetate, methylacetoacetate, ethyl-3-oxovaleriate, 4-hydroxy-2-butanone, ethylpyruvate, 2,3-dichloroacetophenone, acetophenone, 1-[3,5-bis(trifluoromethyl)-phenyl]ethane-1-one, 2-octanone, 2,5-hexanedione, 1,4-dichloro-2-butanone, acetoxyacetone, phenacylchloride, ethyl-4-bromoacetoacetate, 1,1-dichloroacetone, 1,1,3-trichloroacetone and 1-chloroacetone.

8. The process according to claim 5, wherein the liquid, single-phase mixture contains between 35 and 70% by volume of 2-propanol and/or 2-butanol, 9. The process according to claim 6, wherein said amount of the compound of general formula (I) is between 15 and 50% by weight/by volume.

10. The process according to claim 2, wherein said R-specific oxidoreductase is from bacteria.

11. The process according to claim 10, wherein said bacteria is from the group Lactobacillales.

12. The process according to claim 11, wherein said bacteria is from the genus *Lactobacillus*.

13. The process according to claim 2, wherein said R-specific oxidoreductase is from yeast.

14. The process according to claim 13, wherein said yeast is a member of a genus selected from the group consisting of *Pichia, Candida, Pachysolen, Debaromyces* and *Issatschenkia*.

15. The process according to claim 7, wherein said compound of formula (I) is ethyl-4-chloroacetoacetate.

* * * * *